United States Patent
Hedeen et al.

(10) Patent No.: US 6,802,221 B2
(45) Date of Patent: Oct. 12, 2004

(54) SYSTEM AND METHOD FOR CONDITIONED-BASED MONITORING OF A BEARING ASSEMBLY

(75) Inventors: Robert A. Hedeen, Clifton Park, NY (US); Catherine Graichen, Ballston Spa, NY (US); Cecil M. Daniel, Erie, PA (US); Larry R. Handler, Erie, PA (US)

(73) Assignee: General Electric Company, Erie, PA (US)

(*) Notice: Subject to any disclaimer, the term of this patent is extended or adjusted under 35 U.S.C. 154(b) by 88 days.

(21) Appl. No.: 10/108,971

(22) Filed: Mar. 27, 2002

(65) Prior Publication Data

US 2002/0139191 A1 Oct. 3, 2002

Related U.S. Application Data

(60) Provisional application No. 60/279,650, filed on Mar. 29, 2001.

(51) Int. Cl.[7] ............................. G01H 1/08; G01H 1/14
(52) U.S. Cl. ............................ 73/587; 73/593; 73/660
(58) Field of Search ..................... 73/593, 660, 659, 73/579, 587

(56) References Cited

U.S. PATENT DOCUMENTS

| | | | |
|---|---|---|---|
| 4,129,276 A | 12/1978 | Svet | |
| 5,109,700 A | 5/1992 | Hicho | |
| 5,115,671 A | 5/1992 | Hicho | |
| 5,140,858 A | * 8/1992 | Nishimoto et al. | ........... 73/587 |
| 5,381,692 A | 1/1995 | Winslow et al. | |
| 5,446,451 A | 8/1995 | Grosskopf, Jr. | |
| 5,922,963 A | * 7/1999 | Piety et al. | ................ 73/659 |
| 6,053,047 A | * 4/2000 | Dister et al. | ................ 73/593 |
| 6,321,602 B1 | 11/2001 | Ben-Romdhane | |
| 6,499,349 B1 | * 12/2002 | Aronsson | .................. 73/659 |

FOREIGN PATENT DOCUMENTS

JP 61294215 A * 12/1986 ........... F16C/19/52

OTHER PUBLICATIONS

James E. Berry, *How to Track Rolling Element Bearing Health with Vibration Signature Analysis*, Sound and Vibration, Nov., 1991, pp. 24–35, USA.

* cited by examiner

*Primary Examiner*—Hezron Williams
*Assistant Examiner*—Rose M. Miller
(74) *Attorney, Agent, or Firm*—Carl A. Rowold, Esquire; Robert L. Woher, Esquire; Beusse Brownlee Wolter Mora & Maire, P.A.

(57) ABSTRACT

The present invention is for a system (11) or method for conditioned based monitoring of a bearing assembly. The system (11) comprises a sensor (13) placed in proximity to a bearing assembly (12). The sensor (13) generates a signal indicative of the amplitude and frequency of the vibrational movement of the bearing assembly. A process (14) in communication with the sensor (13) receives the signal from the sensor (13) and generates spectral data representative of the bearing vibrational movement. A database (15) comprises data representative of an amplitude threshold, for at least one predetermined frequency, characteristic of a bearing fault. The processor (15) compares the spectral data to the amplitude threshold and generates a signal indication of the bearing assembly.

26 Claims, 6 Drawing Sheets

SYSTEM AND METHOD FOR CONDITIONED-BASED MONITORING OF A BEARING ASSEMBLY

Applicant herein claims priority to the Provisional Patent Application, U.S. Ser. No. 60/279,650, filed Mar. 29, 2001.

FIELD OF THE INVENTION

The present invention relates generally to systems and methods for condition-based monitoring of machines. More specifically, the present invention pertains to the condition-based monitoring of bearing assemblies.

BACKGROUND OF THE INVENTION

In conducting a condition-based maintenance (CBM) program for machines, such as transportation machines of locomotives or other mobile assets, a single analyst using physical evaluation and a knowledge base or database can make a decision on the relative health of various components of the machine. One example of such components includes rotating components, e.g., a bearing.

The basis for determining the presence of bearing defects is the identification of amplitude peaks at certain frequencies in the vibration signature of the bearing.

Equations, known to those skilled in the art, relate the roller diameter, pitch diameter, number of rollers, and contact angle to "fault frequencies" associated with ball, race and cage damage. The presence of these fault frequencies in the vibration spectrum is indicative of bearing damage, and the relative amplitude of the measured parameters and the complexity of the features is a measure of the severity of the damage.

Certain methods of vibrational analysis of bearing machines may assume that various vibrational characteristics, such as the running speed and/or rotating speed are unknown. The frequencies of the bearing fault features are also assumed to be unknown. Moreover, the known geometric characteristics used to calculate fault frequencies are also assumed to be unknown. Accordingly, sample spectra are obtained to identify the various fault features. The data obtained from the sample spectra establish a baseline, or threshold parameters for the machine. However, in the operation of similar machine assets subject to a condition-based maintenance system, the generation of threshold requirements for each individual bearing assembly in the population may not be practical. Moreover, the identification of fault frequencies, running speeds or other operating parameters, may not effectively consider margin of errors that may otherwise be obtained from diagnostics of like bearing assemblies.

BRIEF DESCRIPTION OF THE INVENTION

The present invention is for a system and method for monitoring the condition of a bearing assembly by analyzing spectral data that is representative of the vibrational movement of the bearing assembly. The system generally includes a sensor, such as an accelerometer or vibration sensor, placed in proximity to the bearing assembly. The sensor generates a signal indicative of an amplitude and frequency of the vibrational movement of the bearing assembly. A processor, in communication with the sensor, receives the signals generated by the sensor, and generates spectral data representative of the vibrational movement of the bearing assembly with respect to the amplitude and frequency of the bearing vibrational movement.

A database, in communication with the processor, comprises data representative of a predetermined amplitude threshold for at least one bearing fault, and at least one predetermined frequency (also referred to as a "fault frequency"), wherein each frequency is characteristic of at least one bearing fault. These fault frequencies, and the amplitude threshold, are obtained from spectral data representative of the vibrational movement of a population of like bearing assemblies. In a preferred embodiment, an average overall amplitude is calculated and represents an average vibrational energy measure of the population of like bearing assemblies. The amplitude threshold may be empirically calculated as being contained within some standard deviation of the mean overall amplitude of the population of like bearing assemblies. In addition, the fault frequencies are estimated to appear within certain predetermined ranges of frequencies, based on data obtained from analysis of vibrational movement of the population of bearing assemblies.

Frequencies at which amplitudes exceed the predetermined minimum amplitude threshold and are within a predetermined frequency range for respective fault frequencies are compared to the amplitude threshold in order to evaluate the overall condition of the bearing assembly. The term "peak" may also be used as frequency, such that a peak appears on a spectrum and is characterized by a frequency and an amplitude measurement. In a preferred embodiment, the number of frequencies for each of the respective fault frequencies are counted if their amplitude exceeds the amplitude threshold, or a predetermined multiple thereof. A penalty, representative of a fault feature, is then added to the number of frequencies counted ("peak count"). A score that is representative of the overall condition of the bearing assembly is calculated by a summation of the individual penalties and peak counts. In this manner, a decision relative to the mechanical health of the bearing may be made by comparing features of a vibration frequency spectrum of the bearing to amplitude thresholds that have been determined empirically or statistically by analyzing similar bearing assemblies having similar mechanical and fault characteristics.

In addition, individual scores may be assigned to the different fault frequencies wherein each individual score may be indicative of a specific non-normal condition within the bearing. This capability to capture and evaluate individual scores is important data, which can be used as feedback to the total assembly design agency. Through the identification of such information, the selection and method of installation and manufacture of said bearings may be improved in cases where the quantities and time for production allow.

DETAILED DESCRIPTION OF THE DRAWINGS

Figure 1:
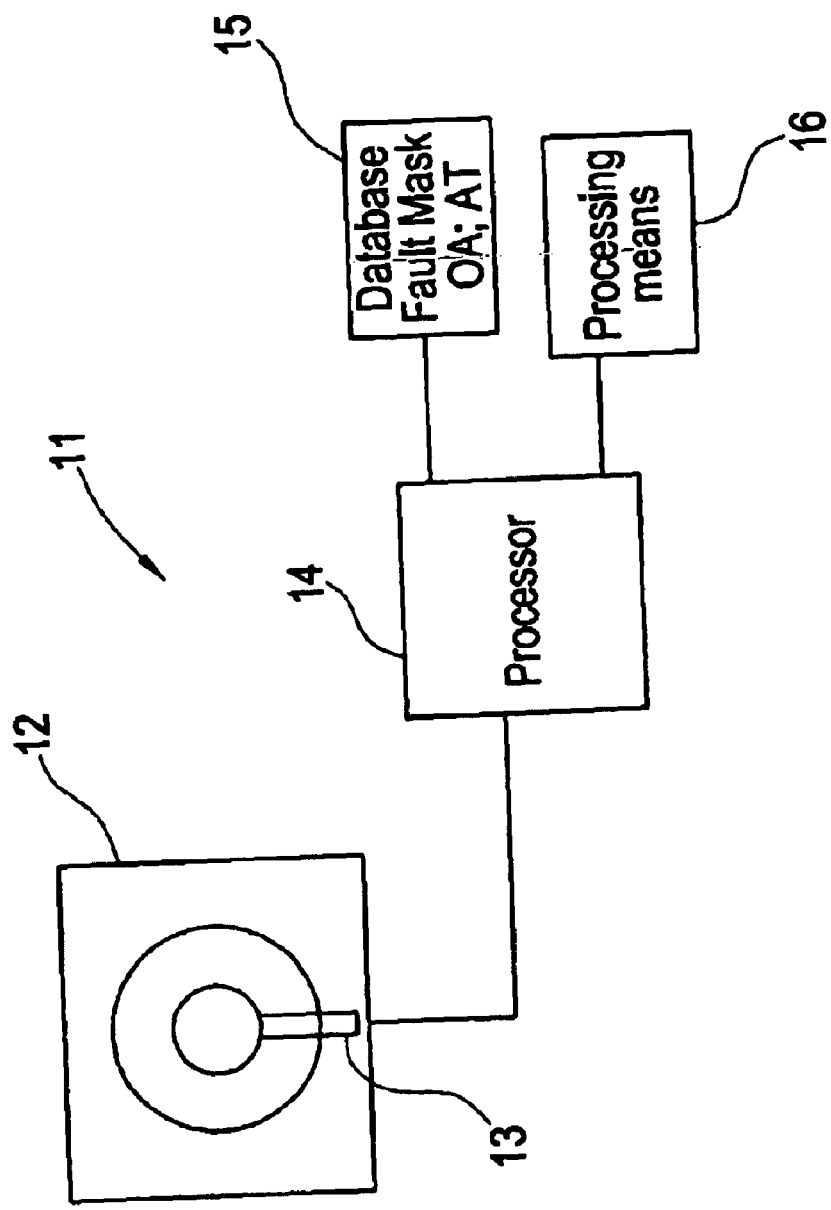
FIG. 1 is a schematic illustrating the present invention for the system.

The present invention for a system and method for the condition-based monitoring of a bearing assembly provides the analysis of spectral data representative of the vibrational movement of a bearing assembly. With respect to FIG. 1 a schematic illustrates the system 11 for the present invention, which includes a sensor 13, such as an accelerometer or vibration sensor, placed in proximity to the bearing assembly 12. The sensor 13 is capable of generating a signal that is indicative of the vibrational movement of the bearing assembly. Such a sensor includes for example, vibrational analysis instruments having accelerometers integrated with processing capabilities for calculating an operating-overall amplitude of the bearing assembly. Such a vibrational analytical instrument includes a VB2000T that may be purchased from CommTest Instruments located in Christchurch, New Zealand.

The sensor 13 is integrated with a processor 14, which receives the signal from the sensor 13 and converts the signal into spectral data illustrative of the vibrational movement of the bearing assembly. The processor 14 may be a typical personal computer and monitor having sufficient memory capacity, and is programmed to display a spectrum, and to interpret and analyze spectral data. The processor 14 may also include networking capabilities to receive or transmit data to remote locations as necessary. The processor 14 provides access to a database 15 for the analysis of the spectral data by a processing means 16.

The above-described components for the present invention of the system operate to provide for the analysis of vibrational movement of bearing assemblies. A description of the operation of these components and the system is provided below. In operation of the present invention, spectral data obtained from an operating bearing assembly 12 is compared to data stored within a database 15 that is representative of vibrational movement of a selected population of bearing assemblies 12. The processor accesses the database 15 that includes a "fault mask" having discrete predetermined frequencies that are characteristic of bearing faults.

Figure 2:
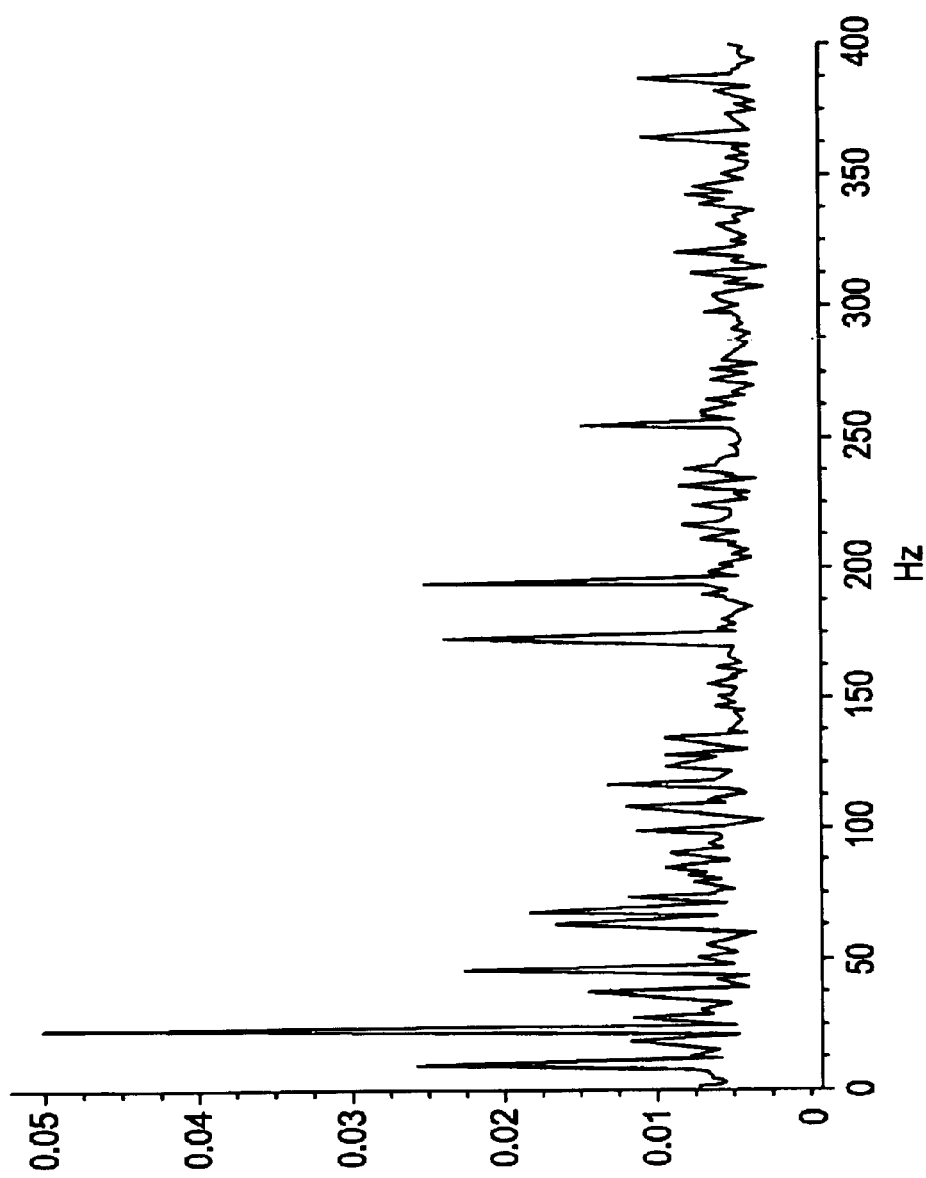
FIG. 2 is a spectrum representative of the vibrational movement of a bearing assembly.

Fault frequencies typically encompass a range of harmonics, e.g., the first 10 or so harmonics of the machinery fundamental rotation speed. For a typical 4-pole electric motor running at around 1800 rpm, the fault frequencies can be expected to lie below 400 Hz. A typical vibration spectrum including bearing fault frequencies is shown in FIG. 2. The amplitude, plotted along the y-axis, may be expressed in any acceptable unit of measurement such as decibels, g/rms or the like. Similarly, while the vibrational movement is generally expressed as a unit of frequency such as Hertz, or cycles per minute, along the x-axis, the vibrational movement can also expressed as a unit of time. Thus, the term amplitude as used in this disclosure includes any unit of measurement capable of describing peak amplitude; and, may be expressed as a function of frequency or time.

The bearing assembly 12 is chosen from a selected population of bearing assemblies, from which fault frequencies have been determined. These predetermined frequencies are previously calculated from the known geometric properties, and operating parameters of the bearing. The following equation provides a formula for calculation of the ball pass frequency on the outer race of the bearing assembly:

$$f = (\eta N/120)(1-[d/D]\cos\phi)$$

The known geometric properties of the bearing and shaft rotational assembly are inserted into this equation to calculate the fault frequency of the bearing assembly 12.

Depending on the nature and severity of the defects, these predetermined frequencies may also be seen as harmonics and as sidebands of the fault frequencies.

Typical frequencies in the fault mask include the first several harmonics of rotation 1×, 2×, etc which are indicative of looseness. Also included would be harmonics of ball pass frequency on the inner and outer race (BPFI and BPFO) and of the ball spin frequency (BSF). In addition, one may include several orders of plus and minus sidebands at 1× and the cage rotation frequency (FTF) about each of the above fault harmonics.

In addition to the fault mask, the database 15 also comprises an amplitude threshold (AT) that represents a minimum amplitude, or some fraction or multiple thereof, at which peaks of a spectrum will be analyzed in order to evaluate the condition of a bearing. The amplitude threshold is calculated from a statistical analysis of the overall amplitude (OA) of each bearing assembly within the population of like bearing assemblies from which the bearing assembly 12 is selected.

The overall amplitude is equal to the square root of the sum of the amplitudes of a given spectrum. The amplitude threshold is calculated using the following equation:

$$AT = OA_{avg} + a\sigma.$$

The term "AT" is amplitude threshold. The $OA_{avg}$ is the average of the overall amplitudes taken from each of a plurality of bearing assemblies defining a population from which the bearing assembly is selected. The term "$a\sigma$" represents a multiple of the standard deviation of the average of the overall amplitude. The multiple "a" is determined empirically, and may vary from population to population.

The processor, using the fault mask data and the amplitude threshold, is programmed to implement an algorithm for identifying "significant peaks" from the spectrum to be analyzed for evaluation of the condition of the bearing assembly. The steps for selecting the significant peaks are set forth in the flow diagram illustrated in FIG. 4. In discussion, generally, the significant peaks include those frequencies (also referred to as "peaks") having an amplitude that is equal to, or greater than, a local spectrum median, or a multiple of the local spectrum median, and that fall within a predetermined frequency range for a respective fault frequency.

Figure 3:
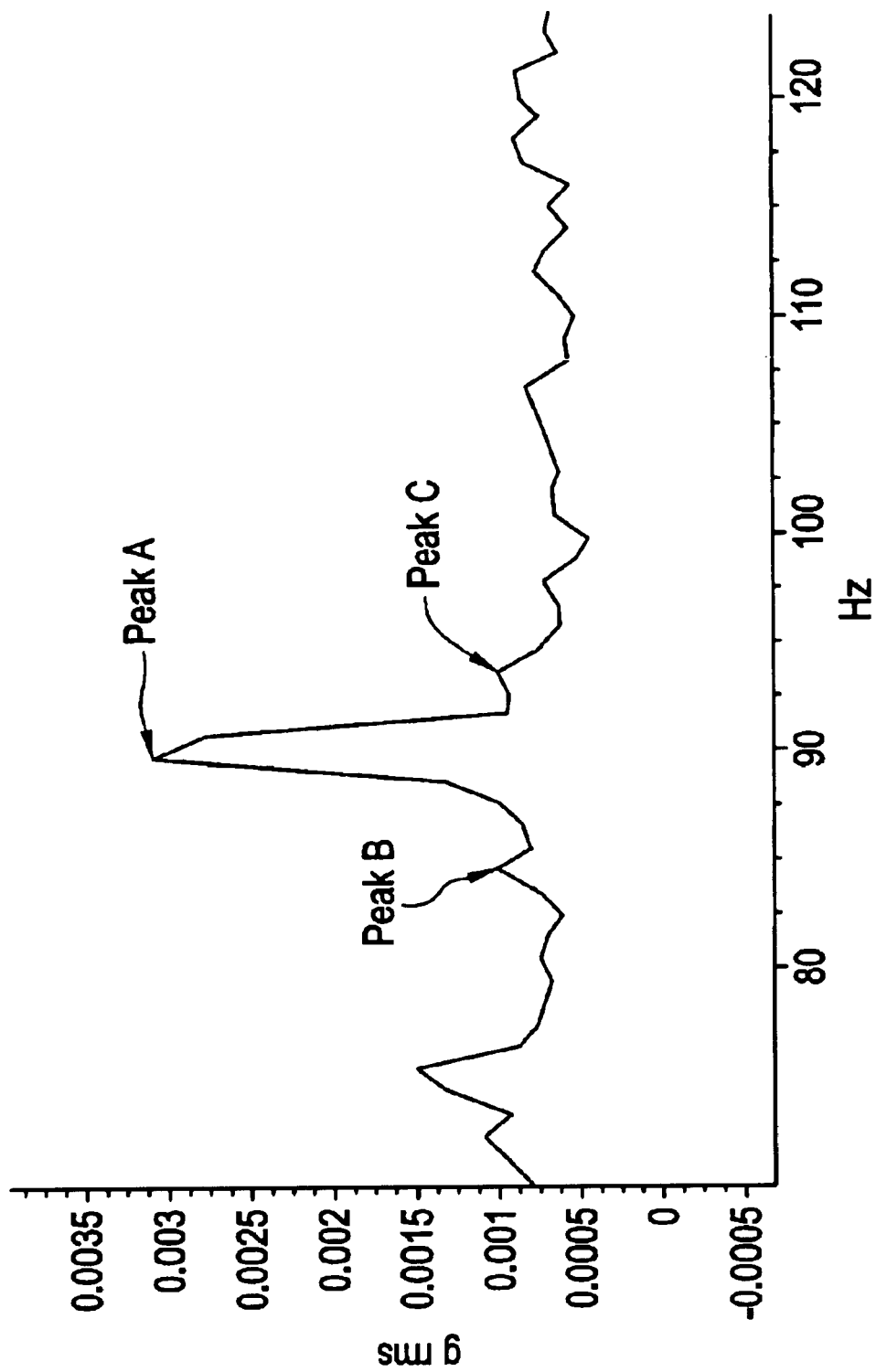
FIG. 3 is an expanded view of a spectrum.
Figure 4:
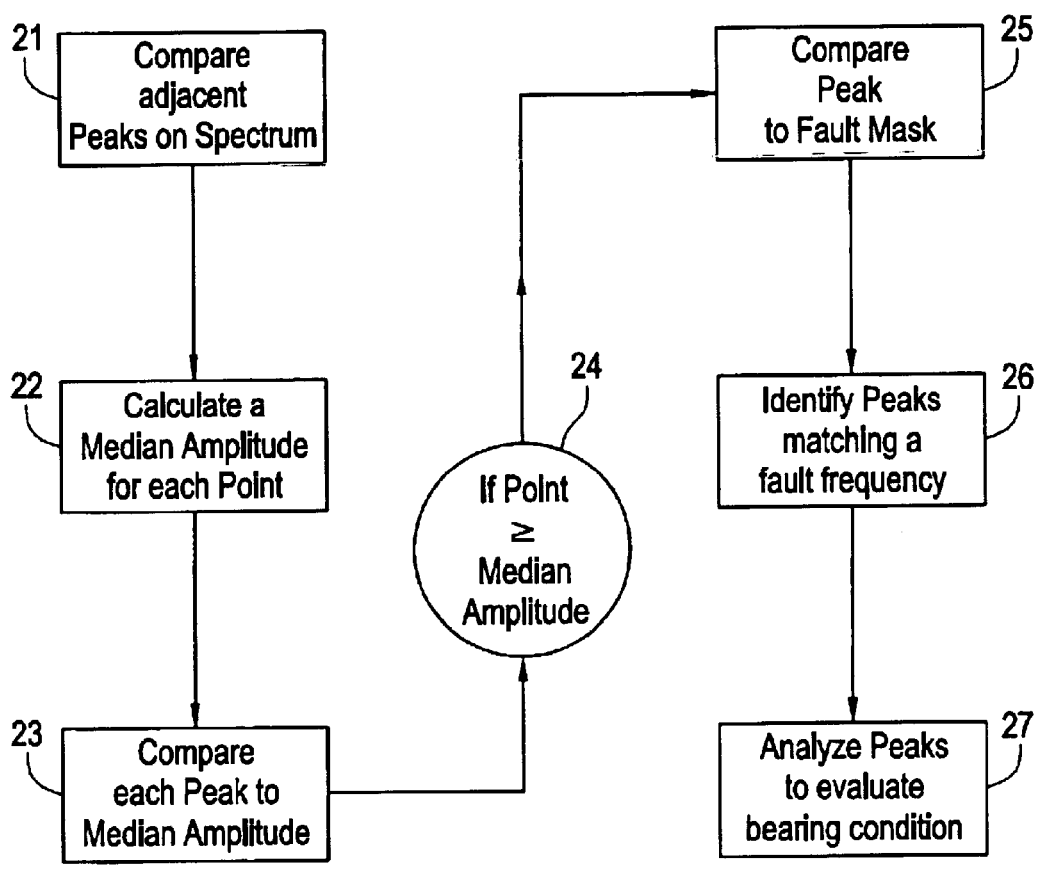
FIG. 4. is a flow diagram illustrating the method of identifying the significant peaks.

The steps for identifying the significant peaks are generally shown in FIG. 4, and explained in more detail herein with reference to the spectrum in FIG. 2 and FIG. 3. The processor 14 is preferably programmed to plot the spectrum as an array of points having two coordinates. In the present case the points on the spectral graph in FIGS. 2 and 3, the x-coordinate is measured in Hertz, and the y-coordinate is listed as amplitude. A spectrum, as shown in FIG. 2, may have 400 points plotted. Each point on the spectrum is evaluated to identify the significant peaks. For purposes describing this of the present invention, the term "peak" may be used to refer to a point on a spectrum having an x-coordinate (Hertz) and a y-coordinate (amplitude).

With respect to step 21 in FIG. 4, a "peak" is selected by comparing a point, peak A, in the spectrum with the point at the previous "x" coordinate, peak B, and the point at the subsequent "x" coordinate, peak C. The peak A, to see if it is peak A local maximum, or has an amplitude greater than both B and C.

In the following step 22, a "local median spectrum" for peak A is then calculated. The local median spectrum is the median amplitude within a range of points on either side of a peak. The range of points must be large enough to include sufficient data and/or a number of peaks to ensure that the proper vibrational signal is collected along with all related and unrelated nearby vibration energy, but small enough not to include nearby large peaks. For example, a range of ±10 points of the point has been found to acceptable for gathering sufficient data for calculation of the median amplitude. In step 24, the peak is compared to the median amplitude of the local spectrum. If the peak is greater than or equal to the local spectrum median, then continue with step 25.

The formula for determining if the peak is significant may require the peak to exceed some multiple of the median to achieve the desired sensitivity to significance. The multiple may be determined empirically or statistically by testing like bearing assemblies to calibrate the multiple median parameter with predetermined significant peak selections. This calculation is done in the processor 14 of FIG. 1 for each frequency measured, and is established through empirical means in order to differentiate it sufficiently in the recorded spectrum.

The significant peaks are then compared to the fault mask and matched to the predetermined frequencies (fault frequencies), in step or means 25 and 26 respectively. If a peak matches a predetermined frequency indicative of a bearing fault feature, the fault feature will be associated with the significant peak and the set of significant fault feature peaks will be analyzed to determine the condition of the bearing. More specifically, if a significant peak falls within a predetermined frequency range within which a fault frequency is expected to fall, then the peak will be analyzed for evaluation of the bearing assembly. The predetermined frequency range is typically derived empirically by considering the likely variation of rotational speed of the like bearing assemblies.

Figure 5:
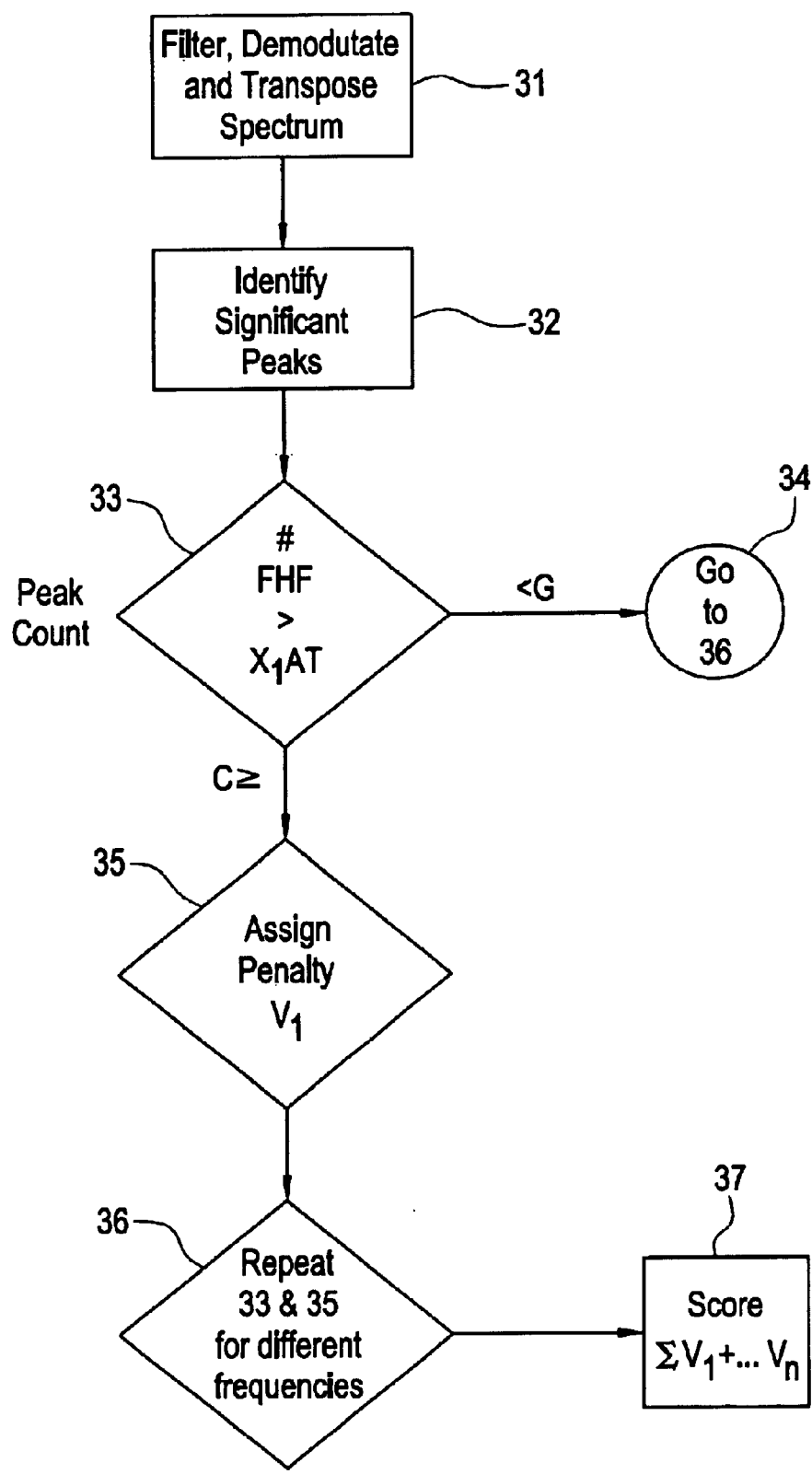
FIG. 5 is a flow diagram of an algorithm for evaluating the condition of a bearing assembly.

The flow chart illustrated in FIG. 5 lays out exemplary steps in the analysis of the spectrum for evaluation of the condition of the bearing assembly. As referenced in block 31, the digitized sensor is high pass filtered (or cropped) to exclude frequencies below the fundamental rotating frequency where extraneous noise may still exist. The spectrum then undergoes a demodulation sequence. Because typical rotating machinery produces vibration from other sources in a given range, a process known as high frequency demodulation is generally employed to extract a vibration spectrum in this range containing solely or primarily bearing faults. The signal is also frequency transposed to a lower frequency range indicative of bearing fault frequencies. These procedures are well known to those skilled in the art, and automated by available vibrational analytical instruments.

With respect to step or means 32, the "significant peaks" in the spectrum are then isolated from the low-level noise between peaks, and identified relative to amplitude and frequency as described above with reference to FIG. 4.

Figure 6:
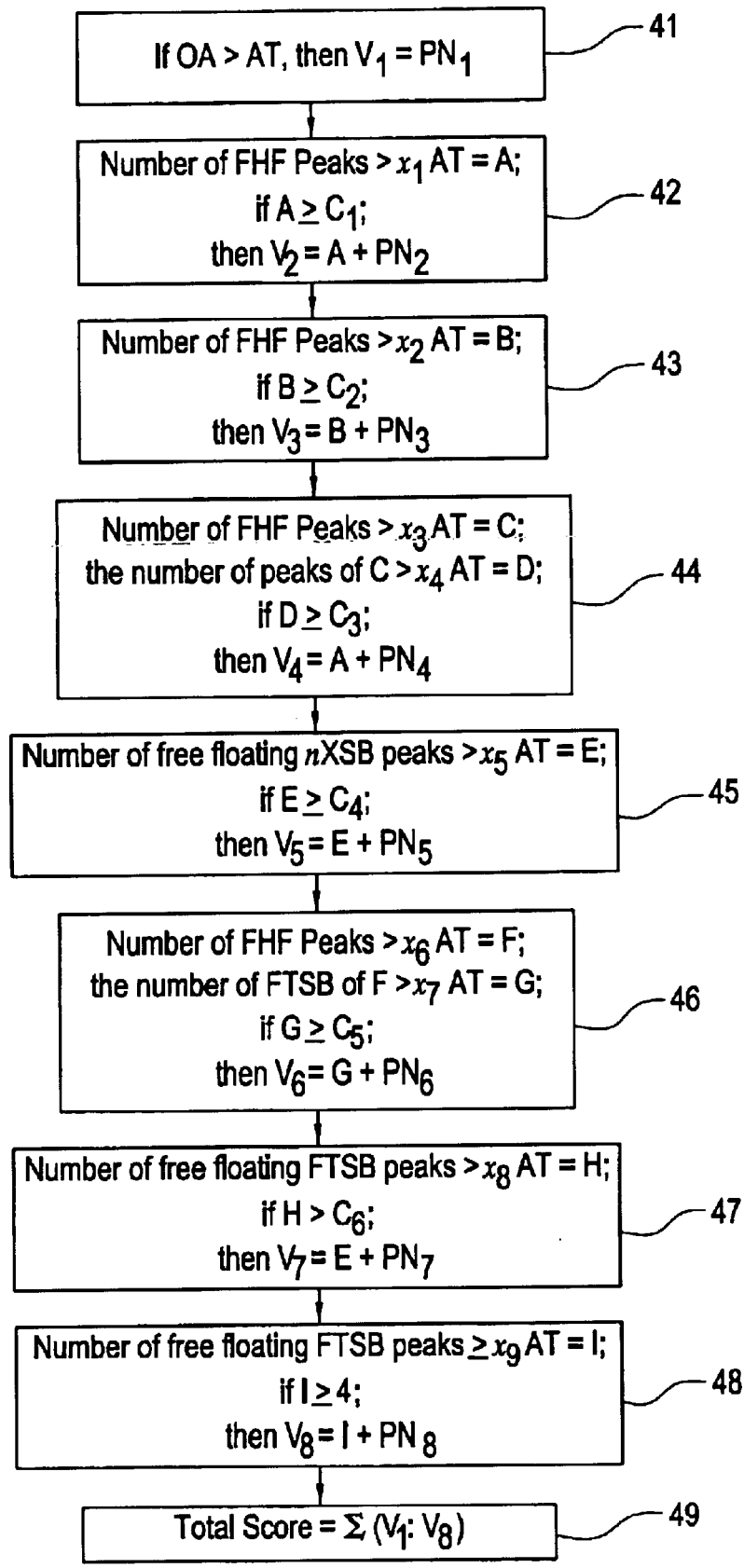
FIG. 6 is a flow diagram of a more detailed algorithm using various frequency types including fault harmonic frequencies, sideband frequencies and fundamental train frequencies, for evaluating the condition of a bearing assembly.

The algorithm illustrated in the flow chart of FIG. 5, sets forth an analysis of fault harmonic frequencies ("FHF"), which includes the peaks at the predetermined frequencies, and the harmonics thereof. The present invention, however, is not limited to fault harmonic frequencies, but may include analysis of various other frequencies, and combination of frequencies, such as sideband (SB) peaks, and fundamental train frequencies (FTF). A more detailed algorithm is illustrated in FIG. 6.

With respect to FIG. 5, in steps 33 through 38, the significant peaks are first compared to a predetermined amplitude threshold (AT). As shown in step or means 33, the number of fault harmonic frequencies (FHF) greater than a predetermined multiple, or fraction, of the amplitude threshold ($x_1AT$) are counted. The "$x_1AT$" is empirically determined as the minimum value of AT (amplitude threshold) above which an FHF peak may appear that may be indicative of a bearing fault. The number of FHF peaks increases the intermediate score. If the number of FHF peaks is greater than or equal to count limit C, then a penalty, "$V_1$", is assigned to the significant FHF peaks as described in step or means 35. The penalty $V_1$ is calculated according to the following algorithm:

the number of FHF peaks>$x(AT)=A$                  1)

If $A \geq C$; then,                  2)

$V_1=A+PN$;                  3)

where A is the peak count exceeding the amplitude threshold (AT), and C is a count limit determined by analysis of the spectra of deteriorated of like bearings The term PN is a "penalty number" that is indicative of the severity of the fault detected. The penalty number is derived through empirical collection of various spectrum characteristics in a sample population, and is indicative of the severity of the type of fault present when considered with respect to the proper functioning of the assembly being measured. The higher the PN, the more critical that feature is to the proper operation.

In step 36, the same process of steps 33 to 35 is repeated for other frequency types and other combination of values of x and C. In a final step or means 37, a score indicative of the overall bearing condition is calculated from the summation of the peak counts and penalties $V_1 \ldots V_n$. The scoring may comprise a sequence of scores indicative of a bearing condition, whereby the more severely damaged the bearing assembly is, the higher the overall score attributed to the bearing condition.

While the foregoing explanation of the present invention refers only to the FHF peaks, other frequencies and combinations of frequencies can be integrated within the analysis. A summation of penalties is illustrated in the flow chart depicted in FIG. 6, which includes additional frequencies, and the "operating" overall amplitude, taken into consideration to determine an overall score.

Sideband peaks (nXSB) are those frequencies include those harmonic frequencies that are 1×, 2× or 3×, of the actual rotational speed of a shaft (not shown) of the bearing assembly 12. These peaks are significant because they are indicative of the contribution of the rotational speed of the bearing shaft. The FTSB peaks are those frequencies at one of the predetermined "rotational speeds" of the group of rolling elements connected within the bearing assembly.

Additional frequencies included in FIG. 6, include free floating sideband peaks are those sideband frequencies that are identified at frequencies within the vibrational spectrum that are not associated with any predetermined frequency characteristic of a bearing fault. The nX peaks include those predetermined frequencies that are identical to a harmonics of the rotational speed of the shaft of the bearing assembly 12.

The reference to the overall amplitude (OA) is representative of an "operating" amplitude of the bearing assembly 12. The operating amplitude is detected using the vibrational analysis instrument and sensor 13, which automates the calculation the operating amplitude. The operating amplitude is then compared to the previously determined amplitude threshold (AT), and a penalty ($V_1$) is assigned for exceeding the amplitude threshold.

The flow diagram in FIG. 6, generally follows the sequence of the flow diagram of FIG. 5. The number of peaks exceeding the AT, or some predetermined multiple or fraction of the AT ($x_1AT \ldots x_9AT$) is compared to a respective count limit ($C_1$ through $C_8$). The peak count (A, B, C, ... I) is added to the score. If the peak count (A, B, C, ... I) exceeds the count limit ($C_1$ through $C_8$), then a penalty number ($PN_1 \ldots PN_8$) is added to the peak count for assignment of a penalty $V_1$. The overall condition is evaluated by adding the penalties, $\Sigma V_1 \ldots V_8$, to determine a total score indicative of the overall condition of the bearing assembly 12. The flow diagram in FIG. 6 is not limited to the sequence of steps disclosed. The steps are not dependant from one another, and may be performed in any sequence.

With respect to steps 42 and 43, fault harmonic peaks are compared to the amplitude threshold providing a peak count that is compared to the peak limits $C_1$ to $C_2$, respectively, and assigned penalties $V_2$ and $V_3$ This is done with two different comparisons/threshold percentages of the AT, in order to properly characterize the extent of damage observed through these readings. Typically the higher value of "x" would have a lower count limit since a higher peak is indicative of more bearing damage.

In step 44, the processor 14 counts the number of sideband peaks of C, which is the number of FHF peaks that exceed an amplitude threshold ($x_3AT$). Then step or means 44, determines the sideband peaks associated with each FHF peak above. The sideband peaks that exceed an amplitude threshold ($x_4AT$) are tallied. If the count of the sideband peaks exceeds the count limit, then a penalty value $V_4$ is added to the score.

Similarly, in step 46 the numbers of fundamental train sideband peaks FTSB for the fault harmonic frequencies that exceed the threshold ($x_6AT$) are counted. The peak count is equal to G, which is then compared to the peak limit $C_5$ If peak count G is greater than the peak limit $C_5$, then a penalty $V_6$ is assigned by adding penalty number 6 to G.

In steps 45, 47 and 48 the number of free floating sideband peaks, free floating fundamental train sideband peaks and the number of peaks exceeding the amplitude threshold are calculated. The penalty values, $V_5$, $V_7$ and $V_8$ are respective assigned by adding the peak counts with penalty numbers $PN_5$, $PN_7$ and $PN_8$ respectively.

The total score is the summation of the peak counts, A through I, and the penalty values $V_1$ through $V_8$. The total score should be indicative of the severity of the bearing condition. That is the higher the score the more severe the damage.

In an alternative embodiment, the algorithm set forth in FIG. 5 and/or FIG. 6, may be conducted separately for each of the various fault features (BPFI, BPFO, BSF, FTF etc.) for respective bearing components. In such a case a penalty may be assessed for each of the various frequencies, and a total score (or a sub-score) may be calculated that is representative of the severity of the a respective fault feature. A total score, including the addition of each of the sub-scores is provided, and indicative of the overall condition of the bearing.

While the invention has been described in what is presently considered to be a preferred embodiment, many variations and modifications will become apparent to those skilled in the art. Accordingly, it is intended that the invention not be limited to the specific illustrative embodiment but be interpreted within the full spirit and scope of the appended claims.

We claim as our invention:

1. A system for monitoring the condition of a roller bearing assembly subject to increasing vibrational movement at characteristic frequencies indicative of bearing assembly faults, the system comprising:

(a) a sensor for detecting vibrational movement of the roller bearing assembly and capable of generating signals indicative of the amplitude and frequency of the vibrational movement of the roller being assembly comprising one or more roller bearing components;

(b) a processor, in communication with the sensor, receiving the signals generated by the sensor and generating spectral data representative of the vibrational movement of the roller bearing assembly with respect to the amplitude and frequency of the roller bearing vibrational movement;

(c) a database, in communication with the processor, comprising data representative of at least one predetermined amplitude threshold for a potential roller bearing fault associated with at least one predetermined frequency, wherein said amplitude threshold and said predetermined frequency for the potential roller bearing fault is obtained from an analysis of spectral data representative of the vibrational movement of a population of like bearing assemblies, and wherein said spectral data comprise peaks having an amplitude and frequency, and said processor identifies the peaks associated with said at least one predetermined frequency for the roller bearing fault, and counts the number of peaks having an amplitude exceeding said amplitude threshold; and, (d) said processor, assigning a score indicative of the number of peaks counted exceeding the amplitude threshold for evaluating the condition of the bearing and generating a signal responsive to the assigned score and to the number of peaks counted having an amplitude exceeding the amplitude threshold and the signal is indicative of the condition of the bearing assembly.

2. The system of claim 1 wherein said database further includes an average overall amplitude obtained from an analysis of spectral data representative of the vibrational movement of said population of the like bearing assemblies and said amplitude threshold is calculated as a deviation from the average overall amplitude.

3. The system of claim 1 wherein the database comprises the step of providing a predetermined frequency indicative of a bearing fault associated with an inner race diameter of the bearing assembly.

4. The system of claim 1 wherein the system comprises the step of providing a predetermined frequency indicative of a bearing fault associated with an outer race diameter of the bearing assembly.

5. The system of claim 1 wherein the database comprises the step of providing a predetermined frequency indicative of a bearing fault associated with roller elements of the bearing assembly.

6. The system of claim 1 wherein the database comprises the step of providing a predetermined frequency indicative of a bearing fault associated with a cage of the bearing assembly.

7. A method for monitoring the condition of a bearing assembly, comprising the steps of:

(a) providing at least one amplitude threshold for a bearing fault;

(b) collecting spectral data, including peaks that are indicative of the amplitude and frequency of the vibrational movement of the bearing assembly;

(c) counting the peaks, of the spectral data, having an amplitude that exceed said amplitude threshold and are associated with at least one predetermined frequency indicative of a bearing fault; and, (d) generating a signal responsive to the number of peaks counted, and indicative of an overall condition of the bearing.

8. The method of claim 7 further comprising the step of assigning a score representative of a number of peaks counted that exceed said amplitude threshold, and evaluating the condition of the bearing assembly based on the score generated.

9. The method of claim 7 further comprising the step of comparing the counted peaks exceeding the amplitude threshold to at least one count limit, and assigning a penalty if the number of peaks counted exceed the count limit, or is equal to the count limit.

10. The method of claim 9 further including the step of assigning a score representative of the number of peaks counted and the assigned penalties, and said score is indicative of the overall condition of the bearing.

11. The method of claim 7 further comprising the step of identifying peaks that are associated with said at least one predetermined frequency indicative of a bearing fault before the step of counting the peaks.

12. The method of claim 11 further comprising the step of providing at least one predetermined range of frequencies associated with said predetermined frequency and said step of identifying peaks comprises the step of selecting only those peaks that are substantially within said at least one predetermined range of frequencies before the step of counting the peaks.

13. The method of claim 12, with respect to those peaks selected, further comprising the step of comparing each selected peak to a local median spectrum, and if a peak is greater than, or equal to the median amplitude of the local spectrum then the peak is compared to the amplitude threshold.

14. The method of claim 7 further including the step of providing an average overall amplitude of the bearing assembly that is representative of the vibrational movement of a selected population of bearing assemblies, and calculating the amplitude threshold as a deviation of said overall amplitude.

15. The method of claim 7 wherein said step of counting frequencies comprises counting harmonic frequencies relative to at least one predetermined frequency.

16. The method of claim 7 wherein the step of counting frequencies comprises counting sideband frequencies relative to at least one predetermined frequency.

17. A method for monitoring the condition of a bearing assembly, comprising the steps of:

(a) providing at least one amplitude threshold for a bearing fault associated with each of a plurality of a bearing components;

(b) collecting spectral data, including peaks, that is indicative of the amplitude and frequency of the vibrational movement of the bearing assembly;

(c) counting the peaks, of the spectral data, having an amplitude that exceed said amplitude threshold and are associated with at least one predetermined frequency indicative of a bearing fault associated with each bearing component; and, (d) generating a signal responsive to the number of peaks counted with respect to each bearing fault and indicative of a condition of the respective bearing components.

18. The method of claim 17 further comprising the step of providing a predetermined frequency indicative of a bearing fault associated with an inner race diameter of the bearing assembly.

19. The method of claim 17 further comprising the step of providing a predetermined frequency indicative of a bearing fault associated with an outer race diameter of the bearing assembly.

20. The method of claim 17 further comprising the step of providing a predetermined frequency indicative of a bearing fault associated with roller elements of the bearing assembly.

21. The method of claim 17 further comprising the step of providing a predetermined frequency indicative of a bearing fault associated with a cage of the bearing assembly.

22. The method of claim 17 further comprising the step of assigning a score representative of a number of peaks counted that exceed said amplitude threshold with respect to each bearing component, and evaluating the condition of each bearing component based on the score generated.

23. The method of claim 17 further comprising the step of assigning a score representative of a number of peaks counted that exceed said amplitude threshold with respect to each bearing component, and evaluating an overall condition of bearing assembly based on all the scores generated.

24. The method of claim 17 further providing an overall amplitude representative of the vibrational movement of a selected population of like bearing assemblies, and providing the amplitude threshold calculated as a predetermined deviation of said overall amplitude.

25. The method of claim 17 wherein the step of selecting frequencies comprises selecting harmonic frequencies relative to the predetermined frequencies.

26. The method of claim 17 wherein the step of selecting frequencies comprises selecting sideband frequencies relative to the predetermined frequencies.

* * * * *